US 8,903,546 B2

(12) United States Patent
Diolaiti et al.

(10) Patent No.: US 8,903,546 B2
(45) Date of Patent: Dec. 2, 2014

(54) SMOOTH CONTROL OF AN ARTICULATED INSTRUMENT ACROSS AREAS WITH DIFFERENT WORK SPACE CONDITIONS

(75) Inventors: Nicola Diolaiti, Palo Alto, CA (US); Paul E. Lilagan, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 850 days.

(21) Appl. No.: 12/541,913

(22) Filed: Aug. 15, 2009

(65) Prior Publication Data
US 2011/0040404 A1    Feb. 17, 2011

(51) Int. Cl.
G06F 19/00    (2011.01)
A61B 19/00    (2006.01)

(52) U.S. Cl.
CPC ....... *A61B 19/2203* (2013.01); *A61B 2019/304* (2013.01); *Y10S 901/14* (2013.01); *Y10S 901/15* (2013.01); *Y10S 901/16* (2013.01); *Y10S 901/41* (2013.01)
USPC ........... 700/245; 700/250; 700/254; 700/262; 700/263; 700/264; 318/568.11; 318/568.2; 318/568.21; 606/130; 901/14; 901/15; 901/16; 901/41

(58) Field of Classification Search
None
See application file for complete search history.

(56) References Cited

U.S. PATENT DOCUMENTS

| | | |
|---|---|---|
| 4,644,237 A | 2/1987 | Frushour et al. |
| 4,791,934 A | 12/1988 | Brunnett |
| 4,831,549 A | 5/1989 | Red et al. |
| 4,837,703 A | 6/1989 | Kakazu et al. |
| 4,979,949 A | 12/1990 | Matsen, III |
| 5,086,401 A | 2/1992 | Glassman et al. |
| 5,230,338 A | 7/1993 | Allen et al. |
| 5,343,385 A | 8/1994 | Joskowicz et al. |
| 5,408,409 A | 4/1995 | Glassman et al. |
| 5,417,210 A | 5/1995 | Funda et al. |
| 5,528,955 A | 6/1996 | Hannaford et al. |
| 5,704,897 A | 1/1998 | Truppe |
| 5,748,767 A | 5/1998 | Raab |
| 5,749,362 A | 5/1998 | Funda et al. |

(Continued)

FOREIGN PATENT DOCUMENTS

| | | |
|---|---|---|
| EP | 812662 A1 | 12/1997 |
| EP | 1125557 A2 | 8/2001 |

(Continued)

OTHER PUBLICATIONS

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 171-1176, vol. 2.

(Continued)

*Primary Examiner* — Jason Holloway
*Assistant Examiner* — Jonathan L Sample

(57) ABSTRACT

An articulated instrument is controllably movable between areas of different work space limits, such as when it is extendable out of and retractable into a guide tube. To avoid abrupt transitions in joint actuations as the joint moves between areas of different work space limits, a controller limits error feedback used to control its movement. To provide smooth joint control as the instrument moves between areas of different work space limits, the controller imposes barrier and ratcheting constraints on each directly actuatable joint of the instrument when the joint is commanded to cross between areas of different work space limits.

20 Claims, 7 Drawing Sheets

(56) References Cited

U.S. PATENT DOCUMENTS

| | | | |
|---|---|---|---|
| 5,755,725 A | 5/1998 | Druais | |
| 5,820,545 A | 10/1998 | Arbter et al. | |
| 5,820,623 A | 10/1998 | Ng | |
| 5,831,408 A | 11/1998 | Jacobus et al. | |
| 5,835,693 A * | 11/1998 | Lynch et al. | 345/473 |
| 5,876,325 A | 3/1999 | Mizuno et al. | |
| 5,950,629 A | 9/1999 | Taylor et al. | |
| 5,987,591 A | 11/1999 | Jyumonji | |
| 6,115,053 A * | 9/2000 | Perlin | 345/475 |
| 6,120,433 A | 9/2000 | Mizuno et al. | |
| 6,184,868 B1 | 2/2001 | Shahoian et al. | |
| 6,204,620 B1 | 3/2001 | McGee et al. | |
| 6,224,542 B1 | 5/2001 | Chang et al. | |
| 6,325,808 B1 | 12/2001 | Bernard et al. | |
| 6,342,889 B1 | 1/2002 | Callahan | |
| 6,371,909 B1 | 4/2002 | Hoeg et al. | |
| 6,398,726 B1 | 6/2002 | Ramans et al. | |
| 6,424,885 B1 | 7/2002 | Niemeyer et al. | |
| 6,442,417 B1 | 8/2002 | Shahidi et al. | |
| 6,456,901 B1 * | 9/2002 | Xi et al. | 700/245 |
| 6,459,926 B1 | 10/2002 | Nowlin et al. | |
| 6,468,265 B1 | 10/2002 | Evans et al. | |
| 6,493,608 B1 | 12/2002 | Niemeyer | |
| 6,522,906 B1 | 2/2003 | Salisbury, Jr. et al. | |
| 6,574,355 B2 | 6/2003 | Green | |
| 6,643,563 B2 * | 11/2003 | Hosek et al. | 700/245 |
| 6,645,196 B1 | 11/2003 | Nixon et al. | |
| 6,659,939 B2 | 12/2003 | Moll et al. | |
| 6,770,081 B1 | 8/2004 | Cooper et al. | |
| 6,837,883 B2 | 1/2005 | Moll et al. | |
| 6,847,922 B1 | 1/2005 | Wampler, II | |
| 6,926,709 B2 | 8/2005 | Bieger et al. | |
| 6,991,627 B2 * | 1/2006 | Madhani et al. | 606/1 |
| 7,041,053 B2 | 5/2006 | Miyake | |
| 7,155,315 B2 | 12/2006 | Niemeyer et al. | |
| 7,181,315 B2 | 2/2007 | Watanabe et al. | |
| 7,194,118 B1 | 3/2007 | Harris et al. | |
| 7,491,198 B2 | 2/2009 | Kockro | |
| 7,725,214 B2 | 5/2010 | Diolaiti | |
| 7,806,891 B2 | 10/2010 | Nowlin et al. | |
| 7,819,859 B2 | 10/2010 | Prisco et al. | |
| 7,963,913 B2 | 6/2011 | Devengenzo et al. | |
| 7,979,157 B2 | 7/2011 | Anvari | |
| 7,996,110 B2 * | 8/2011 | Lipow et al. | 700/245 |
| 8,062,288 B2 | 11/2011 | Cooper et al. | |
| 8,120,301 B2 | 2/2012 | Goldberg et al. | |
| 8,130,907 B2 | 3/2012 | Maurer, Jr. et al. | |
| 8,155,479 B2 | 4/2012 | Hoffman et al. | |
| 8,170,716 B2 | 5/2012 | Coste-Maniere et al. | |
| 8,256,319 B2 | 9/2012 | Cooper et al. | |
| 8,315,720 B2 | 11/2012 | Mohr et al. | |
| 8,335,590 B2 | 12/2012 | Costa et al. | |
| 8,620,473 B2 | 12/2013 | Diolaiti et al. | |
| 2001/0035871 A1 | 11/2001 | Bieger et al. | |
| 2002/0045905 A1 * | 4/2002 | Gerbi et al. | 606/108 |
| 2002/0120188 A1 | 8/2002 | Brock et al. | |
| 2003/0032878 A1 | 2/2003 | Shahidi | |
| 2003/0055410 A1 | 3/2003 | Evans et al. | |
| 2003/0108415 A1 * | 6/2003 | Hosek et al. | 414/783 |
| 2003/0109780 A1 | 6/2003 | Coste-Maniere et al. | |
| 2003/0114730 A1 | 6/2003 | Hale et al. | |
| 2003/0167103 A1 * | 9/2003 | Tang et al. | 700/254 |
| 2003/0225479 A1 * | 12/2003 | Waled | 700/245 |
| 2004/0077940 A1 | 4/2004 | Kienzle et al. | |
| 2004/0106916 A1 | 6/2004 | Quaid et al. | |
| 2004/0238732 A1 | 12/2004 | State et al. | |
| 2004/0249508 A1 * | 12/2004 | Suita et al. | 700/245 |
| 2004/0254679 A1 * | 12/2004 | Nagasaka | 700/245 |
| 2005/0022158 A1 | 1/2005 | Launay et al. | |
| 2005/0054895 A1 | 3/2005 | Hoeg et al. | |
| 2005/0059960 A1 | 3/2005 | Simaan et al. | |
| 2005/0096502 A1 | 5/2005 | Khalili | |
| 2005/0203380 A1 | 9/2005 | Sauer et al. | |
| 2005/0228365 A1 | 10/2005 | Wang et al. | |
| 2005/0251113 A1 | 11/2005 | Kienzle, III | |
| 2006/0142657 A1 | 6/2006 | Quaid et al. | |
| 2006/0258938 A1 | 11/2006 | Hoffman et al. | |
| 2006/0261770 A1 | 11/2006 | Kishi et al. | |
| 2007/0013336 A1 * | 1/2007 | Nowlin et al. | 318/568.21 |
| 2007/0032906 A1 | 2/2007 | Sutherland et al. | |
| 2007/0038080 A1 | 2/2007 | Salisbury, Jr. et al. | |
| 2007/0135803 A1 | 6/2007 | Belson | |
| 2007/0142968 A1 * | 6/2007 | Prisco et al. | 700/245 |
| 2007/0255454 A1 * | 11/2007 | Dariush | 700/245 |
| 2007/0265491 A1 | 11/2007 | Krag et al. | |
| 2007/0270650 A1 | 11/2007 | Eno et al. | |
| 2007/0283970 A1 | 12/2007 | Mohr et al. | |
| 2007/0287884 A1 * | 12/2007 | Schena | 600/104 |
| 2007/0287992 A1 | 12/2007 | Diolaiti et al. | |
| 2008/0004603 A1 | 1/2008 | Larkin et al. | |
| 2008/0033240 A1 | 2/2008 | Hoffman et al. | |
| 2008/0065105 A1 * | 3/2008 | Larkin et al. | 606/130 |
| 2008/0065109 A1 * | 3/2008 | Larkin | 606/130 |
| 2008/0071291 A1 | 3/2008 | Duval et al. | |
| 2008/0081992 A1 | 4/2008 | Kagermeier | |
| 2008/0118115 A1 | 5/2008 | Williamson | |
| 2008/0140087 A1 | 6/2008 | Barbagli | |
| 2008/0161830 A1 * | 7/2008 | Sutherland et al. | 606/130 |
| 2008/0188986 A1 * | 8/2008 | Hoppe | 700/263 |
| 2008/0243142 A1 | 10/2008 | Gildenberg | |
| 2008/0247506 A1 | 10/2008 | Maschke | |
| 2008/0287963 A1 * | 11/2008 | Rogers et al. | 606/130 |
| 2009/0012531 A1 | 1/2009 | Quaid et al. | |
| 2009/0024142 A1 * | 1/2009 | Ruiz Morales | 606/130 |
| 2009/0036902 A1 | 2/2009 | DiMaio et al. | |
| 2009/0088634 A1 | 4/2009 | Zhao et al. | |
| 2009/0192524 A1 * | 7/2009 | Itkowitz et al. | 606/130 |
| 2009/0228145 A1 * | 9/2009 | Hodgson et al. | 700/258 |
| 2009/0248036 A1 | 10/2009 | Hoffman et al. | |
| 2009/0326318 A1 | 12/2009 | Tognaccini et al. | |
| 2009/0326552 A1 | 12/2009 | Diolaiti | |
| 2009/0326553 A1 * | 12/2009 | Mustufa et al. | 606/130 |
| 2009/0326556 A1 | 12/2009 | Diolaiti et al. | |
| 2009/0326711 A1 * | 12/2009 | Chang et al. | 700/248 |
| 2010/0106356 A1 | 4/2010 | Trepagnier et al. | |
| 2010/0198232 A1 | 8/2010 | Diolaiti | |
| 2010/0249657 A1 | 9/2010 | Nycz et al. | |
| 2010/0274087 A1 | 10/2010 | Diolaiti et al. | |
| 2011/0040305 A1 | 2/2011 | Gomez et al. | |
| 2011/0040404 A1 * | 2/2011 | Diolaiti et al. | 700/245 |
| 2011/0071675 A1 * | 3/2011 | Wells et al. | 700/250 |
| 2011/0196199 A1 | 8/2011 | Donhowe et al. | |
| 2011/0202068 A1 | 8/2011 | Diolaiti et al. | |
| 2012/0059391 A1 | 3/2012 | Diolaiti et al. | |
| 2012/0059392 A1 | 3/2012 | Diolaiti | |
| 2013/0231680 A1 | 9/2013 | Diolaiti et al. | |
| 2014/0055489 A1 * | 2/2014 | Itkowitz et al. | 345/633 |

FOREIGN PATENT DOCUMENTS

| | | |
|---|---|---|
| JP | H08154321 A | 6/1996 |
| JP | H11000309 A | 6/1999 |
| JP | 2007029232 A | 2/2007 |
| JP | 2009006410 A | 1/2009 |
| JP | 2009012106 A | 1/2009 |
| WO | WO-2004014244 | 2/2004 |
| WO | WO-2006079108 A1 | 7/2006 |
| WO | WO-2007030173 A1 | 3/2007 |
| WO | WO-2007047782 A2 | 4/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008103383 A1 | 8/2008 |
| WO | WO-2009034477 | 3/2009 |
| WO | WO-2009037576 | 3/2009 |
| WO | WO-2009158164 A1 | 12/2009 |
| WO | WO-2010039394 A1 | 4/2010 |

OTHER PUBLICATIONS

Kapoor, Ankur, *Motion Constrained Control of Robots for Dexterous Surgical Tasks*, Ph.D. Dissertation, The Johns Hopkins University,

(56) References Cited

OTHER PUBLICATIONS

Department of Computer Science, Baltimore, Maryland, Sep. 2007, 351 pages.

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.

Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.

International Search Report and Written Opinion for Application No. PCT/US2012/064379, mailed on Mar. 29, 2013, 12 pages.

International Search Report and Written Opinion for Application No. PCT/US2012/064400, mailed on Mar. 27, 2013, 10 pages.

PCT/US07/71850 International Search Report and Written Opinion of the International Searching Authority, mailed Feb. 13, 2009, 9 pages.

PCT/US09/46234 International Search Report and Written Opinion of the International Searching Authority, mailed Sep. 9, 2009, 13 pages.

PCT/US09/56078 International Search Report and Written Opinion of the International Searching Authority, mailed Jan. 20, 2010, 12 pages.

PCT/US10/28886 International Search Report and Written Opinion of the International Searching Authority, mailed Jul. 6, 2010, 11 pages.

PCT/US10/28897 International Search Report and Written Opinion of the International Searching Authority, mailed Jul. 19, 2010, 16 pages.

PCT/US10/38246 International Search Report and Written Opinion of the International Searching Authority, mailed Sep. 14, 2010, 17 pages.

PCT/US2011/036109 International Search Report and Written Opinion of the International Searching Authority, mailed Oct. 19, 2011, 16 pages.

PCT/US2011/036109 Invitation to Pay Additional Fees and Partial International Search Report, mailed Aug. 18, 2011, 5 pages.

Wei, Guo-Quing et al., "Real-Time Visual Servoing for Laparoscopic Surgery," IEEE Engineering in Medicine and Biology Magazine, Jan./Feb. 1997, pp. 40-45, vol. 16-Issue 1, IEEE.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

\* cited by examiner

SMOOTH CONTROL OF AN ARTICULATED INSTRUMENT ACROSS AREAS WITH DIFFERENT WORK SPACE CONDITIONS

FIELD OF THE INVENTION

The present invention generally relates to controlling articulated instruments in medical robotic systems and in particular, to smooth control of an articulated instrument across areas with different work space conditions.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulated surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulated camera and a plurality of articulated surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

As an operator of a medical robotic system manipulates an articulated instrument across areas with different work space conditions, abrupt changes in joint constraints may occur. For example, as an articulated instrument is extended out of or retracted into a guide tube, such as the entry guide or a cannula, work space conditions for its joints inside, just outside, and well outside the entry guide may differ. Such abrupt changes are generally undesirable, however, since they complicate the operator's control of the articulated instrument.

OBJECTS AND SUMMARY OF THE INVENTION

Accordingly, one object of one or more aspects of the present invention is a medical robotic system and method implemented therein which provides smooth control of an articulated instrument across areas with different work space conditions.

Another object of one or more aspects of the present invention is a medical robotic system and method implemented therein that provides controlled operation of joints of an articulated instrument as the joints encounter different work space conditions.

These and additional objects are accomplished by the various aspects of the present invention, wherein briefly stated, one aspect is a medical robotic system comprising: an articulated instrument having a plurality of joints; an input device; and a controller configured to command actuation of the plurality of joints in response to manipulation of the input device subject to a barrier constraint in which commanded movement of each directly actuatable joint of the plurality of joints from a current area having current work space limits to a new area having new work space limits is prevented until deployment of the plurality of joints satisfies the new work space limits.

Another aspect is a method for controlling a plurality of joints of an articulated instrument, the method comprising: commanding actuation of the plurality of joints in response to manipulation of an input device subject to a barrier constraint in which commanded movement of each directly actuatable joint of the plurality of joints from a current area having current work space limits to a new area having new work space limits is prevented until deployment of the plurality of joints satisfies the new work space limits.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
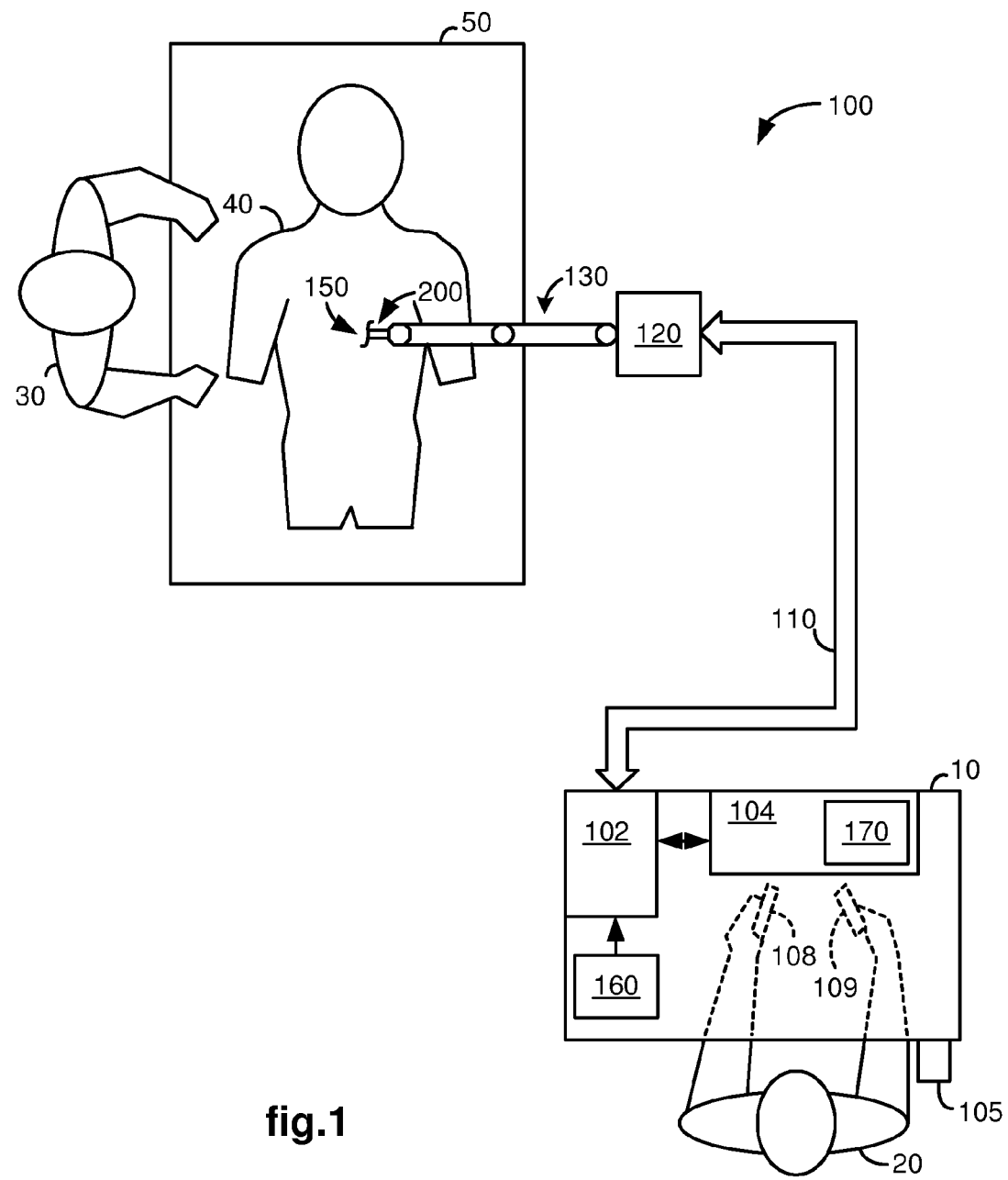
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw about a pivot point located at the entry aperture 150.

The console 10 includes a three-dimensional (3-D) monitor 104 for displaying a 3-D image of a surgical site to the Surgeon, left and right hand-manipulatable input devices 108, 109, and a processor (also referred to herein as a "controller") 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a voice recognition system 160 and a Graphical User Interface (GUI) 170.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 2:
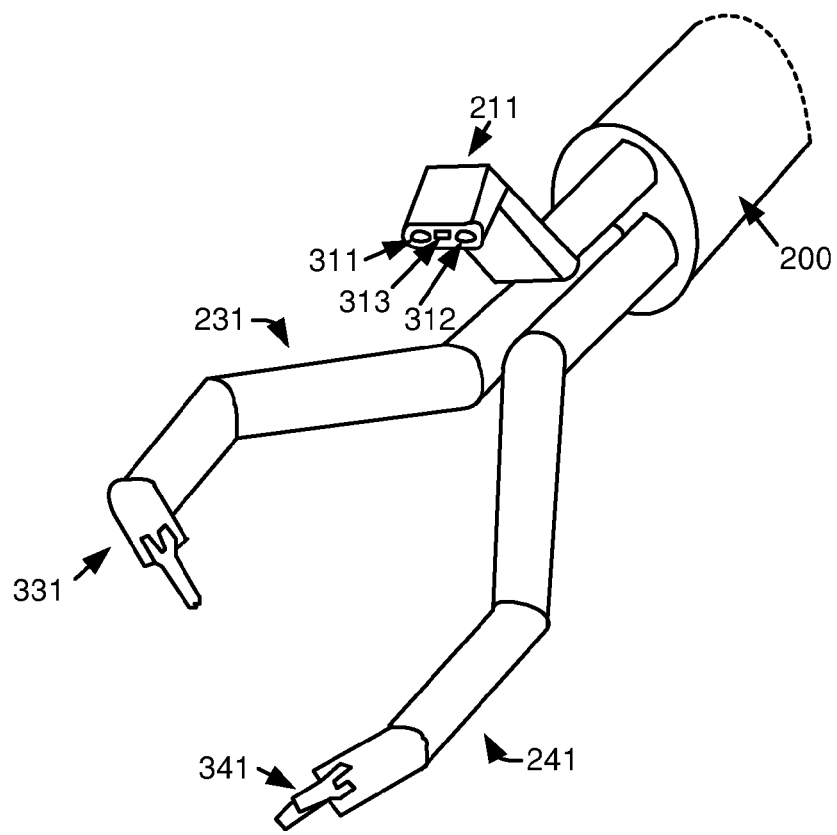
FIG. 2 illustrates a perspective view of a distal end of an entry guide with a plurality of articulated instruments extending out of it in a medical robotic system utilizing aspects of the present invention.
Figure 3:
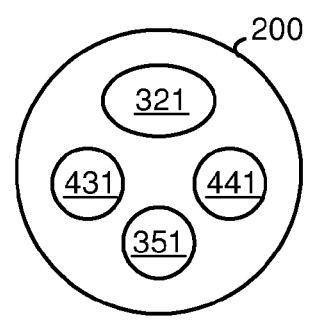
FIG. 3 illustrates a cross-sectional view of an entry guide as used in a medical robotic system utilizing aspects of the present invention.

As shown in FIG. 2, the entry guide 200 has articulated instruments such as articulated surgical tools 231, 241 and an articulated stereo camera 211 extending out of its distal end. The camera has a stereo pair of image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. For example, as shown in FIG. 3, passages 431, 441, 321 are available for extending the tools 231, 241 and camera 211 through the entry guide 200 and out of its distal end. Also, a passage 351 is available for extending another articulated surgical tool through the entry guide 200 and out through its distal end. Each of the surgical tools 231, 241 is associated with one of the input devices 108, 109 in a tool following mode. The Surgeon performs a medical procedure by manipulating the input devices 108, 109 so that the controller 102 causes corresponding movement of their respectively associated surgical tools 231, 241 while the Surgeon views the work site in 3-D on the console monitor 104 as images of the work site are being captured by the articulated stereo camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 transforms the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate devices, such as the tools 231, 241, camera 211, and entry guide 200, that are selectively associated with the input devices 108, 109 at the time. Another function is to perform various methods and implement various controllers described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

Figure 4:
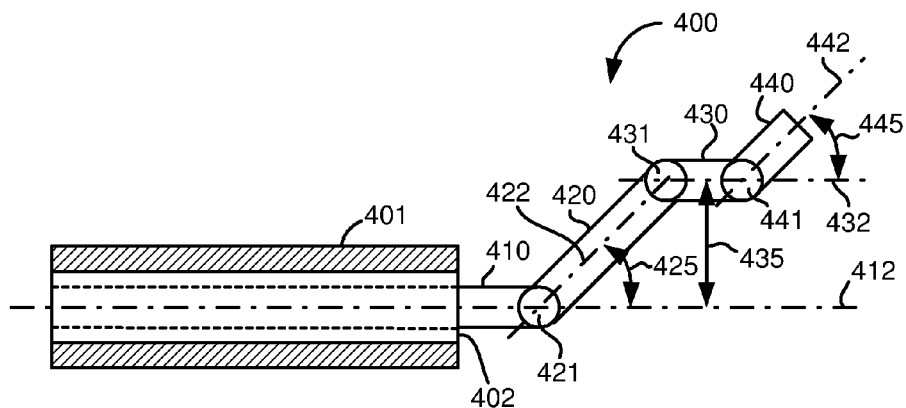
FIG. 4 illustrates a side view of an articulated instrument extending out of a guide tube as used in a medical robotic system utilizing aspects of the present invention.
Figure 13:
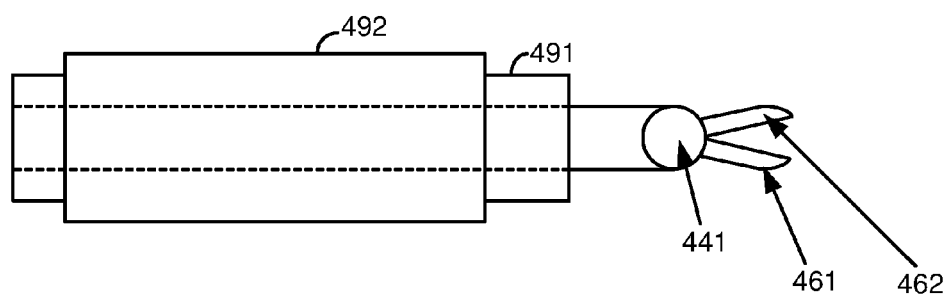
FIG. 13 illustrates a side view of an articulated instrument disposed within an entry guide which in turn, is disposed within a cannula in a medical robotic system utilizing aspects of the present invention.

FIG. 4 illustrates, as a simplified example, a side view of an articulated instrument 400 extending out of a passage 402 of a guide tube 401 as used in the medical robotic system 100. The articulated instrument 400 may be one of the instruments 211, 231, 241, in which case, the guide tube 401 may be the entry guide 200. Alternatively, the articulated instrument 400 may be a separate instrument extending through its own guide tube, in which case, the guide tube 401 may be a cannula. Still, further, the guide tube 401 may be a further distally extending one of an entry guide or cannula when the articulated instrument 400 is inserted in the entry guide, which in turn, is inserted in the cannula (such as shown in FIG. 13). The guide tube 401 may be rigid, controllably flexible, or passively flexible.

In this example, the articulated instrument 400 has an end effector 440, three joints 421, 431, 441, and three links 410, 420, 430 coupled to the joints as shown. Joints 421, 431 (referred to as "joggle joints") are constrained to move together in tandem so that the longitudinal axes 412, 432 respectively of links 410, 430 are always parallel to each other. A distance 435 between the longitudinal axes 412 and 432 is determined by a pitch angle of rotation 425 of the joint 421 about a pitch axis that is perpendicular to the longitudinal axis 412. In addition to being controllably rotated in pitch, the joint 421 may also be controllably rotated in a yaw about a yaw axis that is perpendicular to both the pitch axis and longitudinal axis 412. Although the joints 421, 431, 441 are shown as single joints, each of the joints 421, 431, 441 may comprise a plurality of joints, each of which in turn, provides a different degree-of-freedom movement. For example, the joint 421 may comprise both a pitch joint and a yaw joint that are slightly spaced apart from each other.

In addition to joints 421, 431, 441, two additional joints are provided for manipulating the articulated instrument 400. A roll joint allows the link 410 and consequently, all the joints and links attached to it, to be controllably rotated in roll about the longitudinal axis 412 and a prismatic input/output (IO) joint allows the link 410 and consequently, all the joints and links attached to it, to be controllably translated along the longitudinal axis 412. Since the roll and prismatic joints are dedicated to manipulating the link 410 of the articulated instrument 400, they are referred to herein as also being joints of the articulated instrument 400.

In general, all active joints (i.e., joints controllably movable by an actuator such as a motor) are referred to as being directly actuatable. In the special case of joints constrained so as to move together (such as joggle joints), for the purposes of the method described herein in reference to FIG. 6, however, only the first joint (of the group of constrained joints) which is subjected to barrier and ratcheting constraints is referred to as being directly actuatable and the other joints (of the group of constrained joints) are referred to as being indirectly actuatable.

Figure 9:
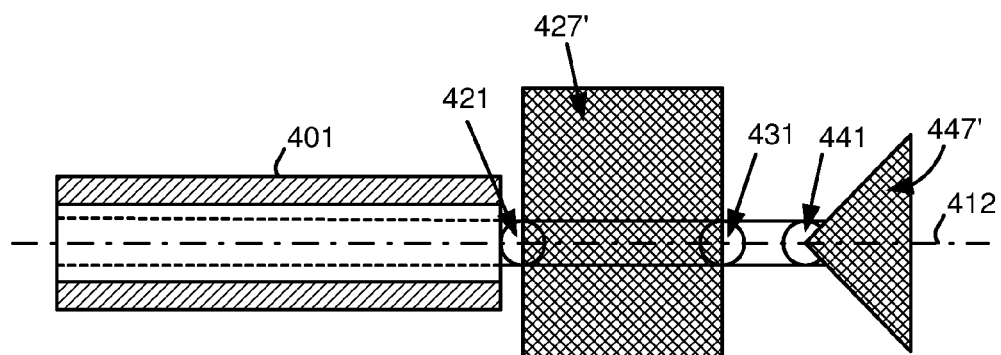

Thus, these five joints and links 410, 420, 430 of the articulated instrument 400 define the dexterous work space of the articulated instrument 400. In particular, movement of joggle joints 421, 431, roll joint and IO joint allows the distal tip of link 430 (referred to as the "joggle tip") to move within a cylinder having the longitudinal axis 412 as its central axis and a maximum allowable length of the distance 435 as its radius. The cylinder in this case is referred to as a work space defined by the joint 421, since actuation of this joint defines the radius of the cylinder. Further, the radius of the cylinder is referred to as a work space variable since the radius defines the size of the cylinder work space. The distal joint 441 (referred to as "wrist joint"), on the other hand, may be controllably rotated in both pitch and yaw directions independently from the joggle joints 421, 431 so that maximum pitch and yaw rotation angle displacements define orthogonal cuts of a cone having the end effector's longitudinal axis 442 as its central axis and the maximum pitch and yaw angles defining its vertex angle. The cone in this case is referred to as a work space defined by the joint 441, since actuation of this joint defines the vertex angle of the cone. Further, the vertex angle of the cone is referred to as a work space variable since the vertex angle of the cone defines the size of the cone work space. Thus, when the joints 421, 431, 441 are all outside of the guide tube 401 where they may be controllably actuated to their maximum rotation angles (i.e., be fully deployable), the joggle tip cylinder 427' and end effector tip cone 447' defining the dexterous work space of the articulated instrument 400 are as shown in FIG. 9.

Figure 5:
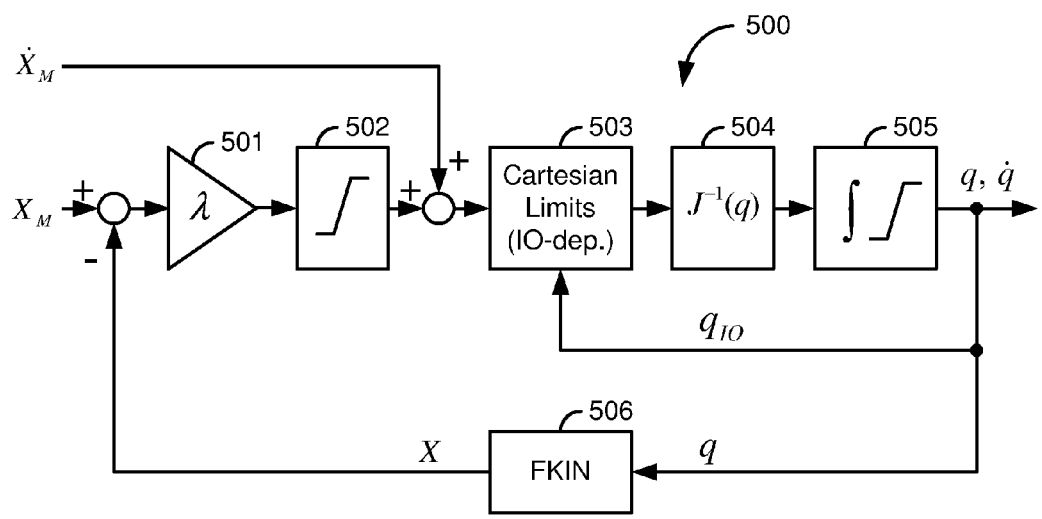
FIG. 5 illustrates a block diagram of an inverse kinematics portion of a master/slave control system in a medical robotic system utilizing aspects of the present invention.

FIG. 5 illustrates, as an example, a block diagram of an inverse kinematics block 500 of a master/slave control system which is implemented in the controller 102 of the medical robotic system 100. The master/slave control system commands and controls actuation of the joints of the articulated instrument 400 in response to operator manipulation of one of the input devices 108, 109 (referred to as the "master") that is associated at the time with the articulated instrument 400.

The inverse kinematics block 500 receives a desired state of the articulated instrument 400 as indicated by Cartesian position "$X_M$" and velocity "$\dot{X}_M$" vectors, which have been generated from sensed joint positions of the master by applying them to the master's forward kinematics along with appropriate scale and offset adjustments. It then processes the desired state of the articulated instrument 400 to generate commanded joint position "q" and velocity "$\dot{q}$" vectors which command actuators (referred to as the "slave") that actuate the joints of the articulated instrument 400.

A current position "X" of the articulated instrument 400 is determined in forward kinematics block 506 by applying sensed joint positions of the articulated instrument 400 to the instrument's forward kinematics. For convenience, FIG. 5 shows the sensed joint position vector and the commanded joint position "q" vector as being the same, even though they may be transiently different due to control system lag, since the current joint positions should be equal to the commanded joint positions at steady-state conditions. A difference between the desired position "$X_M$" and the current position "X" is then multiplied by a gain "λ" in block 501 to generate a Cartesian error "$\lambda(X_M-X)$", which is generally maintained at zero in a well-controlled system. However, when the operator is commanding a position "$X_M$" that is far from the current position "X" of the articulated instrument 400, a large Cartesian error "$\lambda(X_M-X)$" may occur which would cause generating large commanded joint position "q" and velocity "$\dot{q}$" vectors.

Figure 7:
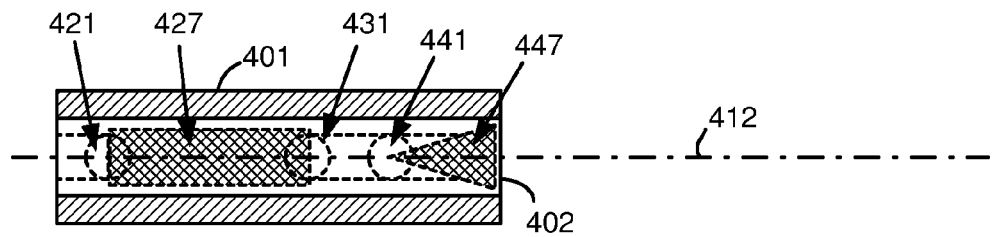
FIGS. 7-9 illustrate a side view of an articulated instrument at various stages as it is extended out of or retracted into a guide tube as used in a medical robotic system utilizing aspects of the present invention.
Figure 14:
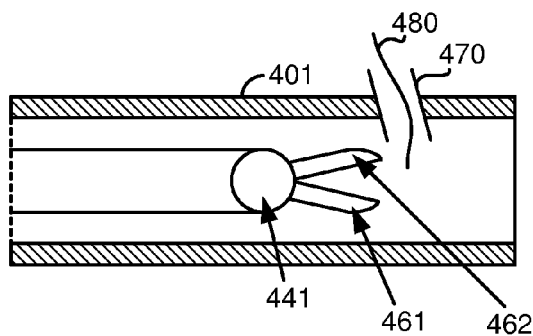
FIG. 14 illustrates a side view of an articulated instrument fully retracted into a laterally fenestrated guide tube in a medical robotic system utilizing aspects of the present invention.

One situation where large Cartesian errors may occur is when the articulated instrument 400 is extended out of the guide tube 401. FIG. 7 illustrates an example where the articulated instrument 400 is fully retracted into the guide tube 401. In this case, the joggle tip cylinder 427 is at a minimum size since the allowed rotation angle of joggle joints 421, 431 inside the guide tube 401 is preferably zero degrees so that instrument links 410, 420, 430 are generally aligned along the instrument's longitudinal axis 412. Likewise, the end effector tip cone 447 is also at a minimum size when the instrument 400 is fully retracted into the guide tube 401. In this case, however, the wrist joint 441 is preferably allowed some movement as space within the passage 402 allows so that its jaws 461, 462 may interact with an object 480 (e.g., grasp a suture) introduced through a lateral fenestration 470 in the guide tube 401 such as shown in FIG. 14.

Figure 8:
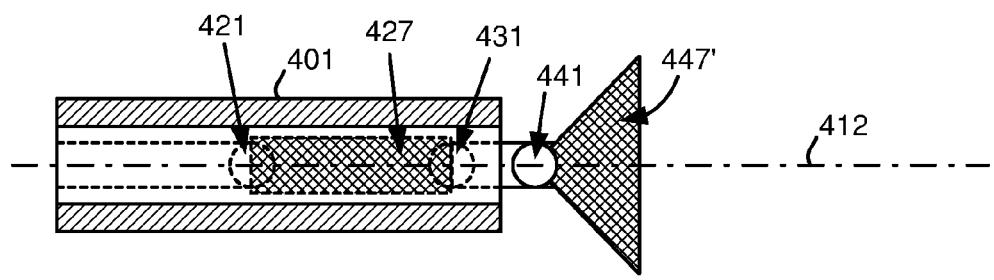

FIG. 8 illustrates an example where the wrist joint 441 of the articulated instrument 400 has been extended out of the guide tube 401 while the joggle joints 421, 431 remain inside. In this case, the joggle tip cylinder 427 remains at its minimum size, but the end effector tip cone 447' expands to its maximum size. Therefore, if the operator is commanding a large wrist movement while the wrist joint 441 is exiting the guide tube 401, because the allowed rotation angle of the wrist joint 441 suddenly changes, a large Cartesian error may occur for the end effector tip component which would cause generating a corresponding large commanded wrist joint position. Such an abrupt change in the control of the end effector tip, however, may be bothersome to the operator. Therefore, it may be desirable in such a case to limit the Cartesian error related to the end effector tip in a limiter block 502 of FIG. 5.

FIG. 9 illustrates an example where joggle joints 421, 431 as well as the wrist joint 441 of the articulated instrument 400 have been extended out of the guide tube 401. In this case, the joggle tip cylinder 427' expands to its maximum size when the joint 421 exits the guide tube 401. At that time, if the operator is commanding a large displacement of the joggle joint tip 430, because the allowed rotation angle of the joggle joints 421, 431 suddenly changes, a large Cartesian error may occur for the joggle joint tip component which would cause generating a corresponding large commanded joggle joint position. Such an abrupt change in the control of the joggle joint tip, however, may be more than bothersome to the operator. It may cause an unexpected jerking action that may be hazardous to the safety of the patient. Therefore, it is desirable in such a case to limit the Cartesian error related to the joggle joint tip in the limiter block 502 of FIG. 5. The limit to the joggle joint tip component of the Cartesian error may be the same as or different than the limit to the end effector tip component of the Cartesian error. In either case, the limits are preferably preset to empirically determined values and programmable by the operator through the GUI 170 so that they may be changed to suit individual preferences of operators.

In the case where the articulated instrument 400 is retracted back into the guide tube 401 from an extended position, a different problem may occur. In this case, the instrument 400 starts from a position where its links 420, 430 may be positioned anywhere in the maximum joggle tip cylinder 427' shown in FIG. 9 and ends up in fully retracted positions where they must now reside in the minimum joggle tip cylinder 427 shown in FIG. 7. As the joint 421 starts to enter the guide tube 401 (as shown in FIG. 9), however, links 420, 430 are unable to follow until they are in their fully retracted positions in which they are generally aligned with the link 410 along the longitudinal axis 412 (as shown in FIG. 7). To avoid commanding the joggle joints 421, 431 to immediately rotate the links 420, 430 to their aligned positions when joint 421 starts to enter the guide tube 401, a more gradual approach is taken to avoid abrupt changes which may prove to be a safety concern if the operator is using the end effector 440 at the time to perform a medical procedure. Thus to avoid such abrupt action, Cartesian limits that are dependent on the position of the joint 421 along the 10 direction (i.e., along the longitudinal axis 412) are imposed in block 503 of FIG. 5.

Figure 6:
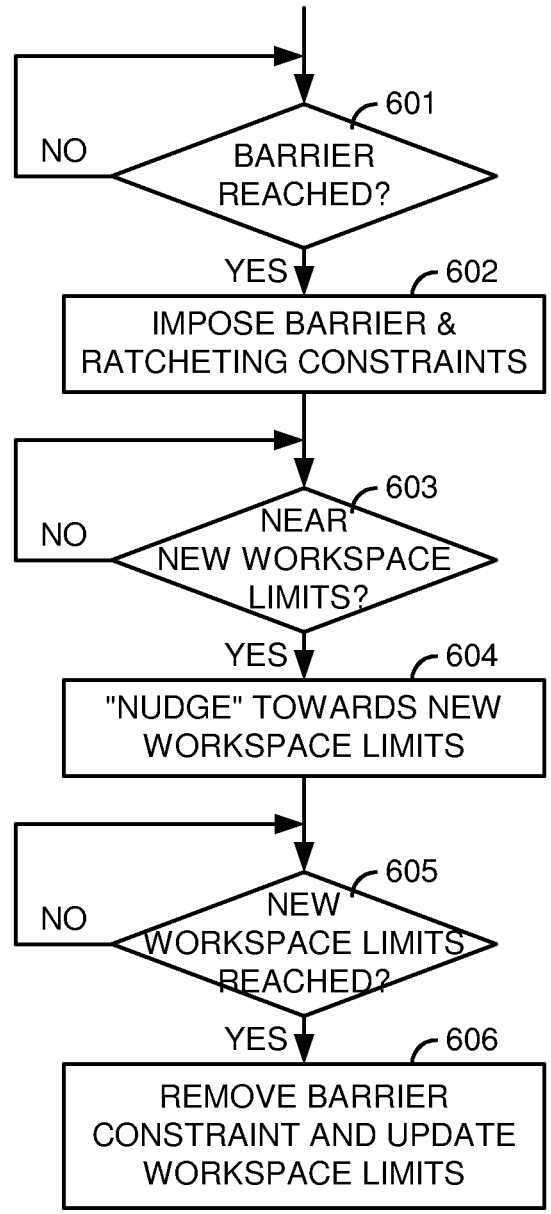
FIG. 6 illustrates a flow diagram of a method for providing smooth control of an articulated instrument as it crosses between areas having different work space limits, utilizing aspects of the present invention.
Figure 10:
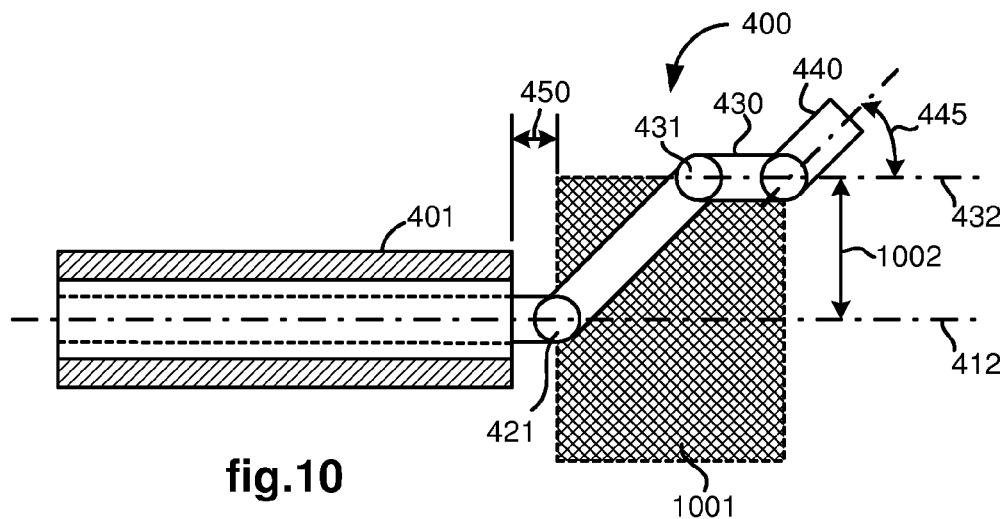
FIGS. 10-12 illustrate a side view of an articulated instrument at various stages as it is retracted into a guide tube as used in a medical robotic system utilizing aspects of the present invention.
Figure 11:
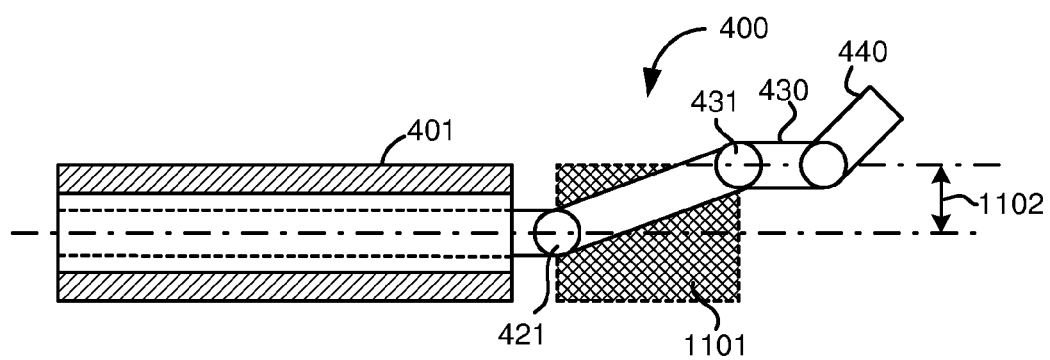
Figure 12:
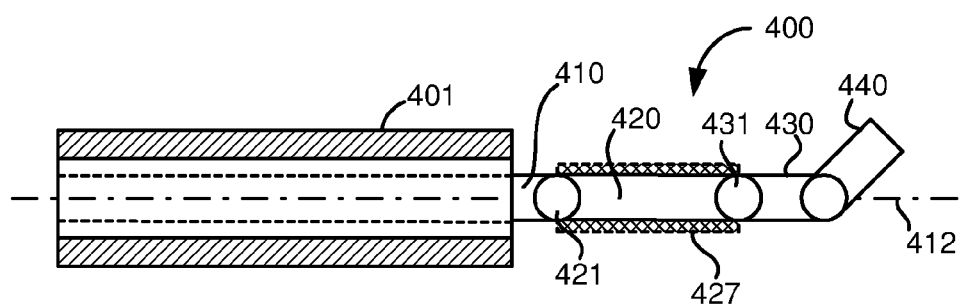

FIG. 6 illustrates, as an example, a flow diagram of a method implemented in block 503 of FIG. 5, for providing smooth control of the articulated instrument 400 as it crosses between areas having different work space limits. To aid in describing the method, the simple example of retraction of the articulated instrument into the guide tube 401 is employed, wherein FIGS. 10-12 illustrate a side view of the articulated instrument 400 at various stages as it is retracted into the guide tube 401.

In 601, the method first determines whether a barrier has been reached. In general, the barrier is at a threshold value from a boundary separating a current area having current work space limits and new area having new work space limits (wherein the current and new work space limits are different). In the present retraction example, the barrier is a position along the longitudinal axis 412 that is a safety margin or threshold distance 450 away from the distal end of the tube guide 401 (such as shown in FIG. 10). The particular threshold distance may be empirically determined so as to provide safe margin and a comfortable feel to the operator. As previously explained, the guide tube 401 may be a further distally extending one of an entry guide or cannula when the articulated instrument 400 is inserted in the entry guide, which in turn, is inserted in the cannula. As an example, FIG. 13 illustrates a side view of the articulated instrument 400 disposed within an entry guide 491 which in turn, is disposed within a cannula 492. Since the entry guide 491 is further extending in the distal direction than the cannula 492 in this case, the entry guide 491 is therefore considered the guide tube 401 for the purposes of the method. In this case, the barrier is determined to have been reached when a directly actuatable joint of the articulated instrument 400 reaches the barrier and is commanded to cross the barrier into an area having different work space limits.

Once the method determines that the barrier has been reached, then in 602, the method imposes barrier and ratcheting constraints on the articulatable instrument 400. Briefly, the barrier constraint prevents commanded movement of each directly actuatable joint of the articulated instrument from a current area having current work space limits to a new area having new work space limits until deployment of the articulated instrument (i.e., its plurality of joints) satisfies the new work space limits. The ratcheting constraint, on the other hand, dynamically alters the current work space limits for a directly actuatable joint so as to approach the new work space limits as the plurality of joints of the articulated instrument are commanded to the deployment that satisfies the new work space limits while commanded movement of the directly actuatable joint from the current area to the new area is being prevented by the barrier constraint.

In the present retraction example, the barrier constraint prevents the joint 421 and consequently, the articulatable instrument 400 from being commanded past the barrier position into the guide tube 401. The ratcheting constraint prevents the distance 435 (i.e., the cylinder work space variable) from increasing beyond its then current distance or equivalently, limiting the commanded rotation of the joint 421 to its current rotation so that the limit continues to get smaller (i.e., ratchet down) as the operator manipulates the master so as to reduce the desired distance of the joggle tip (i.e., link 430) from the longitudinal axis 412 towards its fully retracted position.

FIGS. 10-12 illustrate an example of the "ratcheting" behavior. First, FIG. 10 illustrates the articulated instrument 400 just as the joint 421 reaches the barrier position (i.e., distance 450 from the distal end of the guide tube 401). At this point, the joggle tip cylinder 1001 is limited in size because its radius is limited to the current distance 1002 between the longitudinal axes 412, 432 respectively of links 410, 430 as its radius. Equivalently, at this point the rotation angle of the joint 421 is limited to its current angle of approximately 45 degrees, as opposed to a possible rotation angle of 90 degrees of counter-clockwise rotation from the longitudinal axis 412 which defines the maximum joggle tip cylinder size. Next, FIG. 11 illustrates the articulated instrument 400 after the operator has commanded the current distance to be the shorter distance 1102 (by commanding clock-wise rotation of the joint 421 so that its current angle is approximately 20 degrees instead of the prior 45 degrees), thereby reducing the joggle tip cylinder to the smaller cylinder 1101. Finally, FIG. 12 illustrates the articulated instrument 400 after the operator has reduced the current distance to even more to approximately zero so that the joggle tip cylinder is the minimal cylinder 427 so that the joggle joints 421, 431 and links 420, 430 are aligned with the link 410 along the longitudinal axis 412 and may be freely retracted into the passage 402 of the guide tube 401. Note that the wrist angle 445 is unconstrained throughout this process so that the operator may continue to use the end effector 440 for performing some function even as the joggle joints 421, 431 are being retracted into the guide tube 401.

Referring back to FIG. 6, in 603, the method next determines whether a current deployment of the plurality of joints of the articulated instrument is within a threshold of a deployment that satisfies the new work space limits. In the present retraction example, the new work space limits are defined by the available space inside the passage 402 of the guide tube 401. In particular, in the case of the joggle joints 421, 431, this means the new work space limits (i.e., inside the guide tube 401) require the links 420, 430 to be sufficiently aligned with link 410 so that they can be fully retracted into the guide tube 401. To make this determination, the work space variable defined by the radial distance 435 of link 430 from the insertion axis 412 may be used. Thus, the current deployment of the plurality of joints must be such that the radial distance 435 (which is the radius of the cylinder work space) is within a threshold value of such aligned deployment (e.g., the radial distance 435 is within a threshold value of zero). The particular threshold value used in this case may be empirically determined so as to provide safe margin and a comfortable feel to the operator.

Once the method determines in 603 that the current deployment of the plurality of joints of the articulated instrument is within the threshold value from the deployment that satisfies the new work space limits, then in 604, it causes a force to be felt on the master that "nudges" the operator to move the master towards the deployment that satisfies the new work space limits. A conventional haptic feedback to the master is employed to provide the "nudging" effect. The "nudging" is useful in this case because it may be otherwise difficult for the operator to exactly drive the plurality of joints to the proper deployment that satisfies the new work space limits. One reason for such difficulty is the ratcheting constraint which dynamically alters the current work space limits as the instrument moves toward such deployment.

In 605, the method determines whether the current deployment of the plurality of joints of the articulatable instrument satisfies the new work space limits. In the case of the joggle joints 421, 431 in the present retraction example, this can be determined by using the radial distance 435 as previously explained. In the case of the wrist joint 441, it can be determined by the vertex angle 445, in which case, the deployment satisfies the new work space limits when the angle is zero (i.e., axes 442 and 432 are in alignment). Once the method determines that it has, then in 606, it removes at least the barrier constraint on the joint 421 so that the joggle joints 421, 431 and links 420, 430 may be retracted into the guide tube 401, and updates the current work space limits to be the new work space limits.

As mentioned with respect to FIGS. 10-12, while the joggle joints 421, 431 and links 420, 430 are being retracted into the guide tube 401, the end effector 440 may still be operated and oriented in a normal manner until the wrist joint 441 reaches the barrier. At that point, the method described in reference to 601-606 may then be performed for a work space defined by the wrist joint 441 and end effector 440 (e.g., the cone 447') with the ratcheting constraint now acting on the size of that work space, which in the present example is the end effector tip cone.

Referring back to FIG. 5, after imposing the Cartesian limits in block 503, the desired Cartesian position "$X_M$" and velocity "$\dot{X}_M$" vectors are applied to the inverse Jacobian of the slave in block 504 so that a desired joint velocity "$\dot{q}$" vector may be determined. The output of block 504 is then processed through integrators in block 505 so that a desired joint position "q" vector may be determined. The desired joint position "q" and velocity "$\dot{q}$" vectors are further processed through limiters in block 505 so that they do not exceed their corresponding physical and virtual limitations. The commanded joint position "q" and velocity "$\dot{q}$" vectors provided at the output of block 505 are then used to command actuators for the joints of the articulated instrument 400 in a conventional manner.

Note that the allowed rotation angle for the joints may be changed as joints pass through areas with different work space conditions in block 505 as virtual limits, or equivalently, the sizes of joggle tip cylinders or end effector tip cones corresponding to the allowed rotation angle for the joints may be changed in block 503 as Cartesian limits.

Although the various aspects of the present invention have been described with respect to a preferred embodiment, it will be understood that the invention is entitled to full protection within the full scope of the appended claims.

What is claimed is:

1. A medical robotic system comprising:
an articulated instrument having a plurality of joints;
an input device; and
a controller configured to command actuation of the plurality of joints in response to manipulation of the input device subject to a virtual barrier constraint in which commanded translational movement of a joint of the plurality of joints from a current area in which the joint has current work space limits to a new area in which the joint has new work space limits is prevented until deployment of the joint satisfies the new work space limits, wherein the current and new work space limits are different in at least an allowable range of angular rotation of the joint.

2. The medical robotic system according to claim 1, wherein the controller is configured to command actuation of the plurality of joints in response to manipulation of the input device subject to a ratcheting constraint in which the current work space limits are dynamically altered so as to approach the new work space limits as the joint is commanded to the deployment that satisfies the new work space limits while the commanded translational movement of the joint from the current area to the new area is being prevented by the virtual barrier constraint.

3. The medical robotic system according to claim 2, wherein the controller is further configured to provide a nudging force on the input device when a current deployment of the joint approaches within a threshold of the deployment of the joint that satisfies the new work space limits, to coax an operator of the input device to manipulate the input device so that the controller commands actuation of the joint to the deployment that satisfies the new work space limits.

4. The medical robotic system according to claim 3, wherein the controller is configured to generate the commanded actuation of the using a limited difference between a desired state of the articulated instrument as indicated by manipulation of the input device and a current state of the articulated instrument, and the limit for the limited difference is selected so as to avoid abrupt changes in actuation of the joint as the joint crosses from the current area to the new area.

5. The medical robotic system according to claim 3, further comprising a guide tube, wherein the virtual barrier constraint is performed when the joint is at a threshold distance from a distal end of the guide tube.

6. The medical robotic system according to claim 5, wherein the controller is configured to impose the virtual barrier and ratcheting constraints only when the articulated instrument is being retracted into the guide tube.

7. The medical robotic system according to claim 5, wherein the guide tube is a further extending one of a cannula and an entry guide, wherein the entry guide extends inside the cannula and the articulated instrument extends inside the entry guide.

8. The medical robotic system according to claim 5, wherein the new work space limits are defined by available space in a passage in the guide tube through which the articulated instrument extends.

9. The medical robotic system according to claim 8, wherein the articulated instrument further has a plurality of links coupled together by the plurality of joints, and the new work space limits are defined so that links coupled to joints inside the passage fit within the passage.

10. The medical robotic system according to claim 9, wherein the articulated instrument has an end effector coupled to a wrist joint of the plurality of joints and the new work space limits are defined so as to allow the end effector to interact with an object introduced through a lateral fenestration of the guide tube when the end effector is retracted into the passage of the guide tube.

11. A method for controlling a plurality of joints of an articulated instrument, the method comprising:
commanding actuation of the plurality of joints in response to manipulation of an input device subject to a virtual barrier constraint in which commanded translational movement of a joint of the plurality of joints from a current area in which the joint has current work space limits to a new area in which the joint has new work space limits is prevented until deployment of the joint satisfies the new work space limits, wherein the current and new work space limits are different in at least an allowable range of angular rotation of the joint.

12. The method according to claim 11, wherein the commanding of the actuation of the plurality of is subject to a ratcheting constraint in which the current work space limits are dynamically altered so as to approach the new work space limits as the joint is commanded to the deployment that satisfies the new work space limits while the commanded translational movement of the joint from the current area to the new area is being prevented by the virtual barrier constraint.

13. The method according to claim 12, further comprising:
providing a nudging force on the input device when a current deployment of the joint approaches within a threshold of the deployment of the joint that satisfies the new work space limits, to coax an operator of the input device to manipulate the input device so that the actuation of the joint is commanded to the deployment that satisfies the new work space limits.

14. The method according to claim 13, further comprising:
generating the commanded actuation of the joint using a limited difference between a desired state of the articulated instrument as indicated by manipulation of the input device and a current state of the articulated instrument, wherein the limit for the limited difference is selected so as to avoid abrupt changes in actuation of the joint as the joint crosses from the current area to the new area.

15. The method according to claim 13, wherein the virtual barrier constraint is performed when the joint is at a threshold distance from a distal end of a guide tube through which the articulated instrument at least partially extends.

16. The method according to claim 15, wherein the imposing of the virtual barrier and ratcheting constraints is performed only when the articulated instrument is being retracted into the guide tube.

17. The method according to claim 15, wherein the guide tube is a further extending one of a cannula and an entry guide, wherein the entry guide extends inside the cannula and the articulated instrument extends inside the entry guide.

18. The method according to claim 15, wherein the new work space limits are defined by available space in a passage in the guide tube through which the articulated instrument extends.

19. The method according to claim 18, wherein the articulated instrument further has a plurality of links coupled together by the plurality of joints, and the new work space limits are defined so that links coupled to joints inside the passage fit within the passage.

20. The method according to claim 19, wherein the articulated instrument has an end effector coupled to a wrist joint of the plurality of joints and the new work space limits are defined so as to allow the end effector to interact with an object introduced through a lateral fenestration of the guide tube when the end effector is retracted into the passage of the guide tube.

* * * * *